United States Patent [19]
Gemeinhardt

[11] 3,936,483
[45] Feb. 3, 1976

[54] ORGANIC POLYISOCYANATES
[75] Inventor: Paul G. Gemeinhardt, Pittsburgh, Pa.
[73] Assignee: Mobay Chemical Corporation, Pittsburgh, Pa.
[22] Filed: July 28, 1970
[21] Appl. No.: 64,091

Related U.S. Application Data
[63] Continuation of Ser. No. 358,633, April 9, 1964, abandoned.

[52] U.S. Cl...... 260/453 AR; 252/182; 260/2.5 AT; 260/77.5 AT; 260/453 AM
[51] Int. Cl.² ..................................... C07C 119/048
[58] Field of Search....... 252/182, 102; 260/453 AR

[56] References Cited
UNITED STATES PATENTS
2,683,730  7/1954  Seeger et al. ....................... 260/453
3,294,713  12/1966  Hudson et al. ................... 260/453 X
3,341,463  9/1967  Gemeinhardt ...................... 252/182

FOREIGN PATENTS OR APPLICATIONS
1,348,459  12/1963  France

Primary Examiner—Lewis Gotts
Assistant Examiner—Dolph H. Torrence
Attorney, Agent, or Firm—Gene Harsh

[57] ABSTRACT

A polyisocyanate composition comprising a mixture of from about 10 percent to about 90 percent by weight of toluene diisocyanate and the balance a mixture of polyphenyl-polymethylene-polyisocyanates which latter are preferably the refined condensation product of aniline and formaldehyde. These polyisocyanate compositions are eminently suitable as isocyanate precursors for the production of high rise, thin section cellular polyurethane moldings.

6 Claims, No Drawings

ORGANIC POLYISOCYANATES

This application is a continuation of application Ser. No. 358,633, filed Apr. 9, 1964, now abandoned, and relates to organic polyisocyanates and more particularly to an improved mixture of polyisocyanates which produce polyurethane plastics having improved properties.

It has been proposed heretofore to prepare polyurethane plastics from organic polyisocyantes. Moreover, it is known that mixtures of homologous organic polyisocyanates can be made and used together for reaction with active hydrogen containing compounds to prepare polyurethane plastics. The heretofore known mixtures of homologous polyisocyantes have not always been satisfactory for the production of polyurethane plastics, particularly polyurethane foams, because of unpredictable deficiencies in both the foaming characteristics and in the physical properties of the product. Moreover, some mixtures of homologous polyisocyanates, when reacted with an active hydrogen containing compound produce a discolored polyurethane foam. Discoloration can sometimes be tolerated if it is constant and uniform throughout the reaction mixture. The difficulty with the use of mixtures of polyisocyanates in the production of polyurethane foams is that they have a propensity for causing nonuniform and unpredictable discoloration. This often leads to striations in the resulting product.

It would be desirable in order to obtain uniform color to use a pure toluylene diisocyanate or a pure polyphenyl polymethylene polyisocyanate such as that disclosed in U.S. Pat. No. 2,683,730, but each of these alternatives results in disadvantageous properties in the polyurethane product for different reasons in most cases and the same reason in at least one case. Generally speaking, the dimensional stability and the flame resistance of a polyurethane plastic based on polyphenyl polymethylene polyisocyanate is better than the same properties in a polyurethane based on toluylene diisocyanate. Alternately, the foaming characteristics and the ability to control the reaction are better when using a toluylene diisocyanate. Neither a polyphenyl polymethylene polyisocyanate nor toluylene diisocyanate is entirely satisfactory for foaming in place the cavity where a high rise, thin section molding is desired. The characteristic example is the thin interior space in the wall of a refrigerator. Here the foaming ingredients are inserted into the thin section. They react and rise and fill the cavity with a polyurethane foam. But in the absence of multiple pours which create weak spots, or other processing technique, the foam is sheared and consequently weak at the interface between the wall of the mold and the body of the foam, particularly near the top of the mold. Stated in other words, as the foam prepared from either toluylene diisocyanate alone or polyphenyl polymethylene isocyanate along rises in a thin section mold, the cells near the edge and toward the top of the thin section molding become elongated and very often leave a loose piece of foam between the walls and the upper end of the mold. This causes several difficulties which destroy the value of foaming in place. One difficulty is that the insulation value of the foam is destroyed. Another difficulty is that the foam is then weaker and more friable at the upper end of the thin section molding. Still another difficulty is that dimensional stability is poor at low temperatures, for example below 10° C.

When a polyurethane foam is prepared based on toluylene diisocyanate alone and without the addition of any flame resistant additive, the foam will burn and support combustion once ignited, thus making it unsatisfactory for the production of building materials and the like.

Further, while mixtures of isocyanates which are not homologs have been mentioned in the literature for preparation of polyurethanes, none of these has heretofore proved to be of any practical significance. In many cases the reactivity of the mixture suffers from being in admixture with a non-homolog. The mixture of blends heretofore proposed sometime produce polyurethanes with poorer physical properties than the separate isocyanates. It is very unusual for a mixture of isocyanates to have improved reactivity or to produce improved polyurethanes.

It is therefore an object of this invention to provide an improved mixture of organic polyisocyanates and improved polyurethane plastics prepared therefrom. A further object of this invention is to provide a mixture of organic polyisocyanates for the production of polyurethanes which have improved flame resistance and dimensional stability. Still another object of this invention is to provide a mixture of polyisocyanates which are adapted to the preparation of improved moldable polyurethane plastics. A further object of this invention is to provide a mixture of polyisocyanates adapted to produce a cellular polyurethane plastic, the mixture being such that there is a favorable balance between the rate of foam rise and the rate of gelation of the polymer so that an unusually high rise of foam can be produced with a small amount of shear breakdown of the foam structure at the interface between the foam and the container walls. Still a further object of this invention is the production of polyurethane plastics which have improved physical properties. Another object of this invention is to provide polyurethane foam formulations, particularly adapted for high rise, thin section foaming to produce insulation having improved physical properties throughout.

The foregoing objects and others which will become apparent from the following description are accomplished, generally speaking, by providing a mixture of from about 10 to about 90 per cent by weight of toluylene diisocyanate and the balance polyaryl polyalkylene polyisocyanate, the latter containing both diisocyanate and triisocyanate. Therefore, this invention contemplates mixtures of toluylene diisocyanate and polyaryl polyalkylene polyisocyanates as well as polyurethane plastics prepared therefrom. For best results in the preparation of polyurethane plastics, it is preferred that the mixture of toluylene diisocyanate with polyaryl polyalkylene polyisocyanates have less than 200 ppm and most preferably less than 100 ppm of a heavy metal including compounds of vanadium, chromium, manganese, zinc and gallium, but especially including iron, cobalt and nickel, iron being the worst offender. It is not understood why some heavy metal compounds are detrimental both to the activity of the mixture of isocyanates and to the burning rate of the resulting polyurethane plastic. It may be that some of these heavy metals and their compounds catalyze some of the decomposition reactions which go on in the pyrolysis of a polyurethane foam. It is known that an iron compound in this composition will cause a rapid increase in the burning rate of the foam even at very low concentrations. Thus, it is highly preferred to maintain the iron content of the mixture below about 200 ppm.

The isocyanate mixture of this invention has an exceedingly favorable rate of reactivity when reacted with an organic compound containing at least two active hydrogen containing groups as determined by the Zerewitinoff method between the rate of foam rise and the rate of gelation of the polymer resulting in unusually high rise of the foam while maintaining an unexpectedly small amount of shear breakdown of foam structure at the interface of the foam and the container or mold walls. The mixture is better than either of the essential isocyanates when used alone.

Any suitable mixture of from 10 to 90 per cent by weight of toluylene diisocyanate and the balance a polyaryl polyalkylene polyisocyanate containing both diisocyanates and triisocyanates may be used. The mixture preferably contains at least 50 per cent by weight of the polyphenyl polymethylene polyisocyanate. A preferred mixture is one with less than 200 ppm of a heavy metal and particularly iron which has from 50 to 65 per cent of a polyphenyl polymethylene polyisocyanate containing from about 40 to 60 per cent of a diphenylmethane diisocyanate, from about 20 to 30 per cent of a triisocyanate having the formula:

and the balance high polyisocyanates, with from about 35 to 50 per cent by weight of toluylene diisocyanate which is preferably a mixture of 2,4- and 2,6-toluylene diisocyanate.

Any suitable toluylene diisocyanate may be used including, for example, 2,4-toluylene diisocyanate, 2,6-toluylene diisocyanate and the like. Particularly suitable mixtures are those containing from about 65 per cent to about 80 per cent 2,4-toluylene diisocyanate and the balance 2,6-toluylene diisocyanate. The commercially available mixture containing about 80 per cent 2,4- and about 20 per cent 2,6-toluylene diisocyanate is very useful.

Any suitable polyaryl polyalkylene polyisocyanate and preferably a polyphenyl methylene polyisocyanate which contains both di- and triisocyanates may be used. Mixtures of isocyanates such as those disclosed in U.S. Pat. No. 2,683,730, British Patent 874,430 and Canadian Patent 665,495 are suitable. It is also possible to use mixtures of polyphenyl polymethylene polyisocyanates which are outside the scope of these patents. A particularly desirable one has a viscosity of from about 150 to about 250 cp/25° C., an —NCO content of at least about 31 per cent and has from about 42 per cent to about 48 per cent of its isocyanate content present as a monomeric diphenyl methane diisocyanate. It is preferred to prepare the polyaryl polyalkylene polyisocyanate by the reaction between aniline and formaldehyde in such proportions of these two reactants that an amine product is obtained which has from about 40 per cent to about 60 per cent of diphenylmethane diamine and the balance higher polyamines so that when the resulting mixture of diphenyl methane diamine and higher polyphenyl polymethylene polyamines is phosgenated, the product contains from about 40 per cent to about 60 per cent diphenyl methane diisocyanate, 20 to 30 per cent triisocyanates, 8 to 17 per cent tetraisocyanate and 5 to 30 per cent penta- or higher polyisocyanates. Thus, in accordance with a preferred method of preparing the polyphenyl polymethylene polyisocyanates, one must in fact begin with the aniline-formaldehyde reaction wherein the aniline and acid catalyst are first mixed and reacted together and then the resulting mixture of the acid salt, e.g. aniline hydrochloride, and aniline are reacted with formaldehyde to produce the mixture of diphenyl methane diamine and high polyamines. Then the initial amine product is neutralized with approximately a stoichiometric amount of a base or even a very slight excess of a base such as sodium hydroxide, potasssium hydroxide or the like and then the amines to be phosgenated are separated from the salt formed by decantation and distillation to remove the water and the salt. This mixture of amines may then be phosgenated to prepare a mixture of organic polyisocyanates by any suitable phosgenation reaction such as those disclosed for example of U.S. Pat. Nos. 2,683,160, 2,683,730, 2,875,226 and the like. However, in order to get the desired percentage of diisocyanates, the desired viscosity and the desired —NCO content, it is preferred to carry out the reaction in two stages, first at a temperature of from about —20° C. to about 80° C. and then in a second stage at a temperature of from about 90° C. to about 200° C. Thus, the polyphenyl polymethylene polyisocyanates are preferably prepared by reacting phosgene with the aforementioned mixture of amines in two stages at such a temperature that the exothermic reaction occuring when these two components are combined is initially not substantially above about 90° C. to form a carbamyl chloride-amine hydrochloride slurry which is then reacted with further phosgene at a temperature above about 90° C. but below about 20° C. to prepare the mixture of polyphenyl polymethylene polyisocyanates referred to above. It is preferred to use an inert organic solvent in the phosgenation of the amine. For this purpose, both the amine and the phosgene are premixed with the organic solvent and then reacted in a solution in two stages as set forth above to prepare the organic polyisocyanate. It is preferred to use some type of high speed mixer for contacting the phosgene solution and amine solution in the preparation of the initial carbamyl chloride-amine hydrochloride slurry.

Any suitable high-speed mixer is contemplated by a preferred embodiment of the invention such as, for example, turbo-mixers, colloid mills, pumps including centrifugal pumps, and the like which contain structural elements which rotate at high speeds and thus insure intimate contact between the amine and phosgene within a relatively short period of time. Preferably, the high-speed mixer should be one which rotates at a speed of about 100 rpm or more.

Any suitable organic solvent which is inert to the amine, to the resulting isocyanate and to phosgene may be used. Thus, suitable solvents are, for example, those which have the formula:

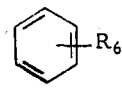

wherein R is the same or different and is lower alkyl, hydrogen, halogen, nitro, aryloxy, alkoxy as well as hydrocarbons, ethers, esters and the like. Any suitable halogen may be used such as, for example, chlorine, bromine, iodine, fluorine and the like. Any suitable aryloxy radical may be used such as, for example, phenoxy, cresoxy, ethylphenoxy, and the like. Any suitable alkoxy radical may be used such as, for example, ethoxy, methoxy, propoxy, butoxy, and the like. Furthermore, mixtures of hydrocarbons such as kerosene may be used. Examples of specific compounds are benzene, toluene, xylene, chlorobenzene, o-dichlorobenzene, nitrobenzene, cyclohexane, durene, o-, m-, p-cymenes, dodecyl naphthylene ethyl acetate, diphenyl and the like.

It has also been found preferable to use a low amount of acid in the condensation of aniline with formaldehyde in order to achieve a mixture of amines which will, on phosgenation, yield the proper amount of diisocyanate, total isocyanate and viscosity as set forth above. This amount is preferably from about 1 per cent to about 15 per cent of the acid required to react with all of the amine in the reaction mixture.

The invention also contemplates polyurethane plastics prepared from these mixtures of organic polyisocyanates. For the production of the polyurethane plastic, any suitable organic compound containing at least two active hydrogen containing groups as determined by the Zerewitinoff method may be used. It is preferred to use polyols and where a cellular polyurethane plastic is to be prepared, it is preferred to use a polyol having from 3 to 8 hydroxyl groups and a molecular weight of from about 200 to about 5,000. The most suitable compounds are prepared by reacting an alkylene oxide such as, ethylene oxide, 1,2-propylene oxide, 1,2-butylene oxide, 2,3-butylene oxide, epichlorohydrin, styrene oxide, or the like with an active hydrogen containing component which preferably has at least three hydrogen atoms which may be reacted with the alkylene oxide to add the alkylene oxide onto the molecule and thus produce a polyhydric polyalkylene ether. The most suitable compounds of the latter type are either polyamines or polyhydric alcohols including for example, ethylene diamine, 2,4-toluylene diamine, 1,3-propylene diamine, 4,4'-diaminodiphenyl methane, p-phenylene diamine, 1,4-butane diamine, 1,6-hexamethylene diamine, trimethylolpropane, glycerine, pentaerythritol, sorbitol, 1,2,6-hexane triol, mannitol, alpha-methyl-d-glucoside and the like. Of course it is also possible when using highly functional organic polyisocyanates to use those active hydrogen compounds which are substantially difunctional such as, for example, polyethylene glycol having a molecular weight of 1500, polypropylene glycol having a molecular weight of 2000 and similar difunctional components which normally produce flexible, foamed polyurethanes when reacted with organic diisocyanates.

It is also possible to use polyesters as the active hydrogen containing compound. For this purpose, any suitable polyester may be used such as are obtained, for example, from polycarboxylic acids and polyhydric alcohols. Any suitable polycarboxylic acid may be used such as, for example, oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, alphahydromuconic acid, beta-hydromuconic acid, alpha-butyl-alpha-ethylglutaric acid, alpha-beta-diethylsuccinic acid, isophthalic acid, terephthalic acid, hemimellitic acid, trimellitic acid, trimesic acid, mellophanic acid, prehnitic acid, pyromellitic acid, benzenepentacarboxylic acid, 1,4-cyclohexanedicarboxylic acid, 3,4,9,10-perylenetetracarboxylic acid and the like. Any suitable polyhydric alcohol may be used such as, for example, ethylene glycol, 1,3-propylene glycol, 1,2-propylene glycol, 1,4-butylene glycol, 1,3-butylene glycol, 1,2-butylene glycol, 1,5-pentane diol, 1,4-pentane diol, 1,3-pentane diol, 1,6-hexane diol, 1,7-heptane diol, glycerine, trimethylol propane, 1,3,6-hexanetriol, triethanolamine, pentaerythritol, sorbitol and the like.

In accordance with a preferred embodiment of the invention a portion, preferably about 20 to 90 per cent and most preferably 30 to 60 per cent by weight of the active hydrogen containing component is one which contains chemically combined phosphorous. Any suitable compound containing active hydrogen containing groups as determined by the Zerewitinoff method and containing chemically combined phosphorous may be used. The phosphorous containing compounds most preferably have free —OH groups and tertiary nitrogen atoms. Suitable examples of phosphorous-containing compounds include de(hydroxyalkyl) alkyl phosphonites, R—P—[O—(R'—O)$_n$H]$_2$, alkyl-di(hydroxyalkyl) phosphinites, RO—P[(R'—O)$_n$H]$_2$, hydroxyalkyl phosphites, P—[O—(R'—O)$_n$H]$_3$, hydroxyalkyl phosphates, PO—[O—(R'—O)$_n$ H]$_3$, and the like where R is lower alkyl or phenyl (examples of lower alkyl are methyl, ethyl, propyl, butyl and the like) and R' is alkylene, preferably having from 1 to 4 carbon atoms, such as methylene, ethylene, 1,2-propylene, 1,2-butylene and the like and $n$ is an integer preferably below 10.

In addition, one may use reaction products of phosphoric acid with a polyhydric alcohol or phosphorous-containing polyols which are prepared by reacting a half ester of an unsaturated carboxylic acid and a polyhydric alcohol with a trialkyl phosphite. It is preferred that phosphorous containing polyols also contain nitrogen and suitable phosphorous-containing polyols which also contain nitrogen having the formula:

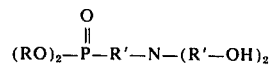

where R and R' have the meanings given above may be used. A preferred compound is dioxyethyl-N,N-bis(2-hydroxyethyl) amino methyl phosphonate,

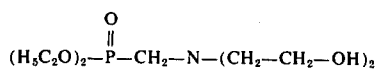

The preferred hydroxyl number for the resin mixture is from about 300 to 600, most preferably 350 – 450 to yield best flame resistance and physical properties including dimensional stability.

In accordance with still another preferred embodiment of this invention, it is possible to chemically combine the phosphorous-containing compound with the above mentioned active hydrogen containing compounds which do not contain phosphorous so that a complete product results which is made up on a weight basis of from 20 to about 90 and preferably 30 to 60 parts of the phosphorous-containing basic structure, the balance being a skeleton of organic compound containing active hydrogen containing groups. Thus, for example, one may take a polyhydric polyalkylene ether, polyester, polythioether, polyamine or the like and react it with one of the phosphorous containing compounds set forth above to prepare a compositie type of product. To illustrate a specific example, one may modify pentaerythritol with both propylene oxide and di-oxyethyl-N,N-bis-(2-hydroxy ethyl amino methyl) phosphonate to prepare a product having an hydroxyl number of from about 200 to about 600 and containing from about 20 to about 90 parts by weight of the phosphonate and the balance pentaerythritol and propylene oxide adduct thereof. It is preferred that these composite phosphorous containing polyols have from 3 to 8 free hydroxyl groups.

When preparing a cellular polyurethane plastic in accordance with the invention, one should provide a blowing agent which causes the reaction mixture to expand by the generation of gas during the isocyanatepolyaddition reaction. The blowing agent may be water which reacts with isocyanate to produce carbon dioxide which blows the reaction mixture. Alternately, a temperature-sensitive blowing agent may be used such as, for example, a halohydrocarbon including trichlorofluoromethane, dichlorofluoromethane, trichlorotrifluoromethane, dichlorodifluoromethane and the like or an alkane such as butane, hexane, heptane, or the like, methylene chloride or any other suitable blowing agent.

It is sometimes desirable to carry out the reaction for the preparation of a cellular polyurethane plastic in the presence of a catlayst. As pointed out above, one should avoid iron compounds where flame resistance is desired. When the polyols used for the reaction contain a tertiary nitrogen atom, it is often not necessary to have any added catalyst. It may be desirable to add a catalyst which may be either a tertiary amine or a tin salt of carboxylic acid. Suitable catalysts of the tertiary amine type include triethylene diamine, tetramethyl quanidine, N,N-diethyl-3-diethylpropyl amine, N-methyl morpholine, N-ethyl morpholine, diethyl ethanol amine, N-coco morpholine, 1-methyl-4-dimethyl aminoethyl piperazine, 3-methoxy-N-dimethyl propyl amine, N-dimethyl-N'-methyl isopropyl propylene diamine, dimethyl benzyl amine, permethylated triamine and the like. Suitable tin salts are stannous octoate, stannous oleate, dibutyltin-di-2-ethyl hexoate and the like.

It is very desirable to have a foam stabilizer present in the course of the reaction and here one may use any suitable foam stabilizer including polydimethyl siloxane and preferably one having a viscosity between about 20 and about 200 centipoises at 25° C. or an alkyl silane polysiloxane polyoxyalkylene block copolymer such as, those disclosed in U.S. Pat. No. 2,834,748. A preferred alkyl silane polysiloxane polyoxyalkylene block copolymer is within the scope of the formula:

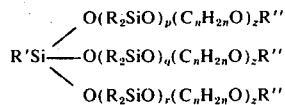

wherein R, R' and R'' are alkyl radicals having 1 to 4 carbon atoms, p, q and r each have a value of from 4 to 8 and $(C_nH_{2n}O)_z$ is a mixed polyoxyethylene oxypropylene group containing from 15 to 19 oxyethylene units and from 11 to 15 oxypropylene units with z equal to from about 26 to about 34.

One may also use sulphonated castor oil as the foam stabilizer substance.

The polyurethane process of the invention may be carried out by simply mixing the organic polyisocyanate with the organic compound containing active hydrogen containing groups. Some of the components may be premixed and it is even possible to pre-react an excess of the organic polyisocyanate with part or all of the organic compound or compounds containing active hydrogen containing groups and then later bring about the foaming reaction. If prepolymers are prepared, they should be prepared under substantially anhydrous conditions. The mixing of the components may be accomplished by stirring with a hand mixer or the mixing may be accomplished by any of the numerous mechanical or spraying devices available including the mixer of U.S. Pat. No. Re. 24,514 and U.S. Pat. No. 3,073,533.

It is also sometimes desirable to include various additives in the reaction mixture such as coloring agents, fillers, flame retardants and the like. Suitable coloring agents are, for example, carbon black, titanium dioxide, menthol blue, chromium red and the like. Suitable fillers are fatty acids including tall oil fatty acids, or tall oil per se, which, if desired, may be halogenated for example, with chlorine or bromine, vermiculite, saw dust, synthetic plastics including vinyl polymers such as, polyvinyl chloride, polystyrene and the like. Suitable flame retardants are antimony oxide, tris(chloroethyl) phosphate, tricresyl phosphate, triphenyl phosphate and the like.

The cellular polyurethane plastics of the invention exhibit some striking advantages over heretofore known cellular polyurethanes, particularly for thin section, high-rise molding. It is possible when using the isocyanate of the invention with a polyol, to prepare a polyurethane plastic which has improved adhesion to the walls of a refrigerator and less elongated cells and reduced shear at the interface between the body of the foam and the refrigerator wall than was heretofore possible. Moreover, the new cellular polyurethanes have greatly improved dimensional stability, particularly at low temperature and a very fine cell structure which gives them a good insulating property. The mixture of polyisocyanates avoids striations and undesirable discoloration. Still further, the mixture is less viscous than heretofore known products containing some impurities resulting from the preparation of polyisocyanates in the phosgenation procedure. There is a striking difference therefore in the way these new polyisocyanates mix with active hydrogen containing compounds. Also, the resulting mixture is relatively non viscous so that it easily flows into all crevices in even a very thin, deep and intricate mold.

The polyisocyanates of the invention are useful in many areas where polyisocyanates have been used heretofore. They are also useful in the preparation of polyurethane plastics for applications not heretofore possible with either of the components of the mixture alone. Furthermore, the particular mixtures of polyisocyanates disclosed result in a foam with less tendency toward discoloration, striation and the like. Thus, the cellular polyurethanes of the invention may be molded into the walls of a dwelling to provide an insulating layer between the outside wall and the inner walls or they may be formed in place in the walls of a refrigerator or the like. Decorative moldings with uniform color can also be made such as Christmas decorations in the form of stars and the like.

The polyisocyanates of the invention offer numerous advantages over the heretofore proposed mixtures of isocyanates as well as the heretofore known unrefined isocyanates, including toluylene diisocyanate and unrefined reaction products of aniline with formaldehyde. In addition to having an exceedingly favorable rate of reactivity for reaction with an organic compound containing active hydrogen containing groups, they produce polyurethanes which have not only self-extinguishing properties, but when used in preferred amounts, produce polyurethanes which are non-burning according to ASTM test D–1692–59T. It is therefore particularly preferred in accordance with the invention to use mixtures which have at least about 35 per cent by weight of polyphenyl polymethylene polyisocyanate and at least about 35 per cent by weight of toluylene diisocyanate. Cellular polyurethane plastics produced from these mixtures of non-homologous polyisocyanates will not only have the excellent reactivity rate and high rise characteristics with low shear, but will be non-burning according to the tests set forth above. The only other isocyanate which will produce the same property of unusually high rise without shear is a mixture of unrefined isocyanates which are only self-extinguishing by the above test and not completely non-burning. The non-burning property together with good compression strength at low temperatures makes the isocyanates of this invention very important from both a physical property view point and a price view point for use in filling the thin walls in refrigerators, including those for domestic use and large industrial installations.

The invention is further illustrated by the following examples in which parts are by weight unless otehrwise specified.

EXAMPLE 1

A polyol mixture is prepared by mixing about 80 parts of a polyhydric polyalkylene ether having an hydroxyl number of about 410 and a viscosity of about 100,000 cp/25°C. prepared by reacting sucrose with propylene oxide, with about 20 parts of dioxy-diethyl-N,N-bis-(2-hydroxyl ethyl) amino methyl phosphonate. An isocyanate mixture is prepared by mixing about 50 parts of 80 per cent 2,4- and 20 per cent 2,6-toluylene diisocyanate with about 50 parts of a polyphenyl polymethylene polyisocyanate prepared by phosgenating the reaction product of aniline with formaldehyde, said polyphenyl polymethylene polyisocyanate having the following formula:

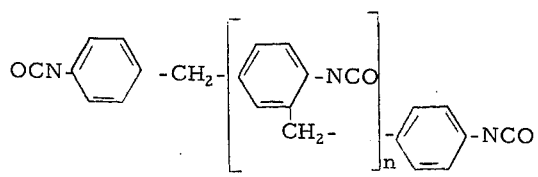

wherein $n$ has an average value of about 1.1 and contains about 45 per cent diisocyanate, about 20 per cent triisocyanate, the balance being tetra- and pentaisocyanates sufficient to give $n$ a value of about 1.1, said polyphenyl polymethylene polyisocyanate having an —NCO content of about 31.7. Then about 100 parts of the polyol mixture and about 82.4 parts of the premixed isocyanates are combined wiht about 30 parts of trichloromonofluoromethane, about 1.5 parts of N,N,N′,N′-tetramethyl-1,3-butane diamine and about 1 part of an alkyl silane siloxane oxyalkylene block copolymer having the formula:

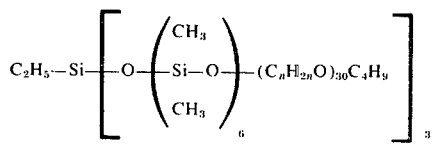

wherein $(C_nH_{2n}O)$ is a mixed polyoxyethylene and oxypropylene block copolymer containing about 17 oxyethylene units and 13 oxypropylene units on a machine mixer as disclosed in U.S. Pat. No. Re. 24,514. The mixture from the foam machine is discharged into a cardboard mold where it begins to cream in about 10 seconds and rises to produce a rigid cellular polyurethane plastic in about 135 seconds. The maximum exotherm during the foaming reaction is about 164° C. After curing at room temperature for 8 hours or more, a rigid cellular polyurethane plastic results which has a density of about 1.6 lbs/ft$^3$ and has a compression strength at yield of 20.5 lbs/in$^2$. The foam is non-burning according to ASTM test D–1692–59T.

EXAMPLE 2

About 80 parts of a polyhydric polyalkylene ether having an hydroxyl number of about 440 and a viscosity of about 45,000 cp/25° C. prepared by reacting alpha-methyl glucoside with propylene oxide are premixed with about 20 parts of dioxy-diethyl-N,N-bis-(2-hydroxy ethyl) aminomethyl phosphonate (OH number 440). About 100 parts of the mixture of polyols is then mixed with about 87 parts of the mixture of isocyanates employed in Example 1, about 30 parts of trichloromonofluoromethane, about 1.5 parts of 1-methyl-4-dimethyl amino ethyl piperazine and about 1 part of the alkyl silane siloxane oxyalkylene block copolymer of Example 1 on a machine mixer as disclosed in U.S. Pat. No. Re. 24,514. The mixture from the foam machine is discharged into a cardboard mold where it begins to cream in about 10 seconds and rises to produce a rigid cellular polyurethane plastic in about 135 seconds. The maximum exotherm during the foaming reaction is about 172° C. After curing at room temperature for 8 hours or more, a rigid cellular polyurethane plastic which has a density of about 1.5 lbs/ft$^3$ and has a compression strength at yield of 17 lbs/in$^2$ results. The foam is non-burning according to ASTM test D–1692–59T.

EXAMPLE 3

About 100 parts of the polyol mixture of Example 1 are mixed with about 119 parts of the isocyanate mixture of Example 1, about 3 parts of water, about 1.5 parts of N,N,N′,N′-tetramethyl-1,3-butane diamine and about 1 part of the alkyl silane siloxane oxyalkylene block copolymer of Example 1 on a machine mixer as disclosed in U.S. Pat. No. 24,514. The mixture from the foam machine is discharged into a cardboard mold where it begins to cream in about 5 seconds and rises to produce a rigid cellular polyurethane plastic in about 105 seconds. The maximum exotherm during the foaming reaction is greater than about 200° C. After curing at room temperature for 8 hours or more, a rigid cellular polyurethane plastic which has a density of about 2.1 lbs/ft$^3$ results. The foam is non-burning according

EXAMPLE 4

About 100 parts of the polyol mixture of Example 1 are mixed with about 93.5 parts of a mixture of isocyanates prepared by mixing about 20 parts of 80 per cent 2,4- and 20 per cent 2,6-toluylene diisocyanate with about 80 parts of the polyphenyl polymethylene polyisocyanate of Example 1, about 30 parts of trichloromonofluoromethane, about 1.5 parts of N,N,N', N'-tetramethyl-1,3-butane diamine and about 1 part of the alkyl silane siloxane oxyalkylene block copolymer of Example 1 on a machine mixer as disclosed in U.S. Pat. No. Re. 24,514. The mixture from the foam machine is discharged into a carboard mold where it begins to cream in about 15 seconds, and rises to produce a rigid cellular polyurethane plastic in about 200 seconds. The maximum exotherm during the foaming reaction is about 155° C. After curing at room temperature for 8 hours or more, a rigid cellular polyurethane plastic which has a density of about 1.8 lbs/ft$^3$ results. The foam is non-burning according to ASTM test D–16-92–59T.

EXAMPLE 5

Example 1 is repeated except that in place of 82.4 parts of the mixture of isocyanates, 72.5 parts of a mixture of isocyanates prepared by combining 80 parts of 80 per cent 2,4- and 20 per cent 2,6-toluylene-diisocyanate and 20 parts of the polyphenyl polymethylene polyisocyanate of Example 1 are used. The mixture begins to cream in about 7 seconds and rises to produce a rigid cellular polyurethane plastic in about 130 seconds. The maximum exotherm during the foaming reaction is about 185° C. After curing at room temperature for 8 hours or more, a rigid cellular polyurethane plastic which has a density of about 1.5 lbs/ft$^3$ results. The foam is self-extinguishing according to ASTM test D–1692–59T.

EXAMPLE 6

Example 1 is repeated except that in place of 82.4 parts of the isocyanate mixture one uses 92 parts of a mixture of 40 parts of 80 per cent 2,4- and 20 per cent 2,6-toluylene diisocyanate with 60 parts of the polyphenyl polymethylene polyisocyanates of Example 1. The mixture begins to cream in about 13 seconds and rises to produce a rigid cellular polyurethane plastic in about 185 seconds. The maximum exotherm during the foaming reaction is about 160° C. After curing at room temperature for 8 hours or more, a rigid cellular polyurethane plastic results which has a density of about 1.7 lbs/ft$^3$. The foam is non-burning according to ASTM test D–1692–59T.

EXAMPLE 7

Example 1 is repeated except that in place of the 82.4 parts of the mixture of isocyanates, one employs 78 parts of a mixture of isocyanates prepared by mixing about 60 parts of a mixture of 80 per cent 2,4- and 20 per cent 2,6-toluylene diisocyanate with about 40 parts of the polyphenyl polymethylene polyisocyanate of Example 1. The mixture begins to cream in about 9 seconds and rises to produce a rigid cellular polyurethane plastic in about 155 seconds. The maximum exotherm during the foaming reaction is about 170°C. After curing at room temperature for 8 hours or more, a rigid cellular polyurethane plastic results which has a density of about 1.6 lbs/ft$^3$. The foam is non-burning according to ASTM test D-1692-59T.

EXAMPLE 8

About 100 parts of a polyester prepared from a mixture corresponding to about 2.5 mols of adipic acid, 0.5 mol of phthalic anhydride and 4.1 mols of 1,2,6-hexanetriol having an hydroxyl number of about 280, a molecular weight of about 800 and a viscosity of about 2500 cp/73° C. is mixed with about 54.7 parts of the mixture of isocyanates of Example 1, about 30 parts of trichloromonofluoromethane, about 2.5 parts of N-ethyl morpholine and about 2.5 parts of dimethyl amineoleate on a machine mixer as disclosed in U.S. Pat. No. Re. 24,514. A substantially rigid foam having a density of approximately 2 lbs/ft$^3$ is obtained.

EXAMPLE 9

A composition suitable for coating wood, metal or the like is prepared by combining 100 parts of a polyester prepared from about 15.6 mols of adipic acid, about 16.3 mols of diethylene glycol and about 1 mol of trimethylol propane, said polyester having a molecular weight of about 2000 and an hydroxyl number of about 56 are mixed with about 10.5 parts of the mixture of polyisocyanates of Example 1 in about 100 parts of the diethyl ether of diethylene glycol. The resulting solution may be coated on wood where it cures to a hard chemically resistant coating.

EXAMPLE 10

About 100 parts of a polyester prepared from adipic acid and ethylene glycol and having a molecular weight of about 2000 and an hydroxyl number of about 56 are prereacted with about 21 parts of the mixture of isocyanates of Example 1 to prepare a prepolymer having free —NCO groups. About 100 parts of the resulting prepolymer is then mixed with about 3.75 parts of 1,4-butane diol under substantially anhydrous conditions and cast in a mold where it is allowed to cure to prepare a substantially non-porous polyurethane casting.

EXAMPLE 11

About 100 parts of a polyester prepared by reacting adipic acid, diethylene glycol and trimethylol propane to an hydroxyl number of about 50 are mixed with about 37.4 parts of the mixture of isocyanates of Example 1, about 2.5 parts of N-ethyl morpholine, about 1.5 parts of dimethyl amino oleate, about 1.5 parts of sulphonated castor oil and about 3.2 parts of water on a machine mixer as disclosed in U.S. Pat. No. Re. 24,514. The resulting foam after curing is flexible and has a low density.

EXAMPLE 12

About 100 parts of a polyhydric polyalkylene ether prepared by reacting glycerine with propylene oxide until a product is obtained having an hydroxyl number of about 56 are mixed with about 38 parts of the mixture of isocyanates of Example 1, about 0.3 part of stannous octoate, about 0.5 part of 1-methyl-4-dimethyl aminoethyl piperazine, about 1 part of N-methyl morpholine, about 1 part of the alkyl silane siloxane oxyalkylene block copolymer of Example 1 and about 3.2 parts of water on a machine mixer as disclosed in U.S. Pat. No. Re. 24,514. The resulting mixture is discharged into a mold where it rises and cures in a short time to form a cellular polyurethane plastic having a low density.

EXAMPLE 13

The mixture of toluylene diisocyanate and polyphenyl polymethylene polyisocyanate used in the foregoing working examples is prepared as follows:

The polyphenyl polymethylene polyisocyanate is prepared in a separate step beginning with aniline hydrochloric acid and formaldehyde to prepare a mixture of amines which is subsequently phosgenated. An aqueous solution of 36 per cent hydrochloric acid is reacted with aniline in a first step in such proportions that about 12.5 per cent of the stoichiometric quantity of hydrochloric acid required to react with the amino groups is used. The resulting mixture of aniline-hydrochloride and aniline is adjusted to a temperature of about 50° to about 55° C. and a 37 per cent formaldehyde solution in water is added to the mixture of aniline and aniline-hydrochloride solution. The aniline-aniline hydrochloride solution is agitated throughout the addition of the formaldehyde solution. After the addition of all of the formaldehyde solution, the temperature of the reaction mixture is increased to about 100° C. and digested at this temperature with agitation for about two hours. Approximately a stoichiometric amount of a concentrated sodium hydroxide solution is then added to neutralize the digested product which consists of a mixture of amines containing about 47 per cent diamine and higher polyamines obtained by the condensation of the aniline with the formaldehyde. The residual water, salt and aniline are separated from the amine product to obtain a substantially anhydrous mixture of amines which is phosgenated in the following manner to prepare a mixture of polyisocyanates. A 15 per cent solution of the resulting mixture of amines in monochlorobenzene is mixed in a highly agitated reaction mixture with a 15 per cent solution of phosgene in monochlorobenzene. The proportions of the reactants are such that there is about 150 per cent excess of phosgene in the reaction mixture of diisocyanate required to react with all of the amino groups in the reaction mixture to produce an isocyanate. The reaction temperature in the initial stage is held at about 50° C. with cooling. The initial product is then transferred to a second reaction vessel where it is heated with additional phosgene at a temperature of about 130°C. for about one hour to complete the reaction. The final product is obtained by removing the solvent and the hydrochloric acid under conditions which do not exceed about 165° C. After purification by removal of the HCl and solvent, a mixture of polyisocyanates is obtained which corresponds to the following formula:

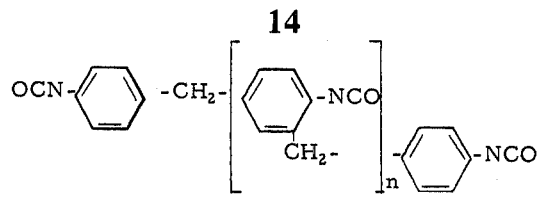

wherein $n$ has an average value of 1.1 and contains about 45 per cent diphenyl methane diisocyanate, about 20 per cent triisocyanate, about 15 per cent tetraisocyanate and about 20 per cent penta- or higher polyisocyanates, the product having a viscosity of about 200 cp/25°C., a pour point of about 0° F. and containing about 31.5 per cent free —NCO.

The iron content of the resulting mixture of isocyanates is determined by polarographic analysis to be about 200 ppm. The iron content is reduced to about 25 ppm or 50 ppm as desired by contacting the mixture of isocyanates with at least about 10 per cent by weight of decolorizing activated carbon with agitation over night. The activated carbon is filtered off and the resulting mixture again analyzed where the iron content is 25 ppm or 50 ppm depending on the time of agitation and the efficiency of the activated carbon.

The resulting polyphenyl polymethylene polyisocyanate is then mixed with 80 per cent 2,4- and 20 per cent 2,6-toluylene diisocyanate in the amounts shown in the following table to prepare the mixture of isocyanates contemplated by the present invention.

Table 1

|  | Isocyanate Type | | | | |
| --- | --- | --- | --- | --- | --- |
|  | 1 | 2 | 3 | 4 | 5 |
| Polyphenyl polymethylene isocyanate (parts) | 50 | 80 | 20 | 60 | 40 |
| 80% 2,4- and 20% 2,6-toluylene diisocyanate (parts) | 50 | 20 | 80 | 40 | 60 |
| NCO, percent | 40 | 35 | 45 | 38.3 | 41.7 |
| Amine equivalent | 104.8 | 119.7 | 93.4 | 109.5 | 100.5 |
| Viscosity, cp/25° C. | 20 | 75 | 10 | 50 | 25 |
| Hydrolyzable chlorides, percent | 0.3 | 0.5 | .05 | 0.3 | 0.3 |
| Total chlorides, percent | 0.5 | 0.7 | 0.1 | 0.5 | 0.5 |
| Acidity, percent | 0.2 | 0.2 | .01 | 0.2 | 0.2 |
| Iron, ppm | 50 | 50 | 25 | 50 | 50 |

It is to be understood that the foregoing working examples are given for the purpose of illustration and that any other suitable mixture of polyaryl polyalkylene polyisocyanates with toluylene diisocyanate, active hydrogen containing compound, catalyst, stabilizer or the like could have been used in the examples provided that the teachings of this disclosure are followed.

Although the invention has been described in considerable detail in the foregoing it is to be understood that such detail is merely for the purpose of illustration and that many variations can be made by those skilled in the art without departing from the spirit and scope of the invention except as set forth in the claims.

What is claimed is:

1. A composition comprising a mixture of from about 10 per cent to about 90 per cent by weight of toluylene diisocyanate selected from the group consisting of 2,4-toluylene diisocyanate, 2,6-toluylene diisocyanate and mixtures thereof and the balance a polyphenyl-polymethylene-polyisocyanate comprising a mixture of from about 40 per cent to about 60 per cent diphenylmethane diisocyanate, from about 20 per cent to about 30 per cent of triisocyanate having the formula

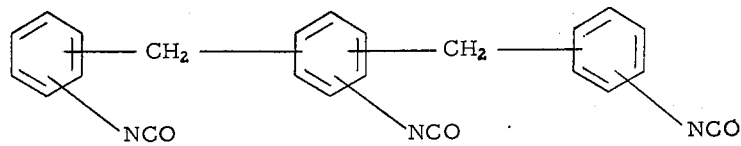

and the balance higher functional polyphenyl-poltmethylene-polyisocyanates.

2. The composition of claim 1 wherein the toluylene diisocyanate is an isomeric mixture of about 80 per cent 2,4-toluylene diisocyanate and about 20 per cent 2,6-toluylene diisocyanate.

3. The composition of claim 2 wherein the toluylene diisocyanate component is present in an amount of from about 50 per cent to about 35 per cent by weight and the polyphenyl-polymethylene-polyisocyanate component is present in an amount of from about 50 per cent to about 65 per cent by weight.

4. The composition of claim 2 wherein the toluylene diisocyanate component is present in an amount of about 50 per cent by weight component the polyphenyl-polymethylene-polyisocyanate compound is present in an amount of about 50 per cent by weight.

5. The composition of claim 1 wherein the polyphenyl-polymethylene-polyisocyanates are represented by the formula

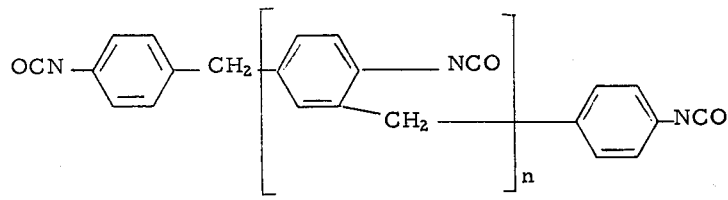

wherein $n$ has an average value of 1.1 and the mixture contains about 45 per cent diphenylmethane diisocyanate, about 20 per cent triisocyanate, about 15 per cent tetraisocyanate and about 20 per cent penta- or higher functional polyisocyanates, the mixture having a viscosity of about 200 cp/25°C., a pour point of about 0°F. and about 31.5 per cent free —NCO.

6. The composition of claim 1 wherein the higher functional polyphenyl-polymethylene-polyisocyanate comprises from about 8 per cent to about 17 per cent tetraphenylene trimethylene tetraisocyanate and from about 5 per cent to about 30 per cent higher frunction homologous polyphenyl-polymethylene-polyisocyanates.

* * * * *

UNITED STATES PATENT AND TRADEMARK OFFICE
CERTIFICATE OF CORRECTION

PATENT NO. : 3,936,483
DATED : February 3, 1976
INVENTOR(S) : Paul G. Gemeinhardt It is certified that error appears in the above-identified patent and that said Letters Patent are hereby corrected as shown below:

Column 5, line 64, correct --alpha-hydromuconic-- so that it appears as a hyphenated word;

Column 6, line 63, delete "complete" and insert --composite--;

Column 7, line 30, correct the spelling of --catalyst--;

Column 9, last line, correct the spelling of --with--;

Column 10, line 60, the patent should be identified as --U.S. Patent No. Reissue 24,514--;

Column 15, Claim 1, line 21, correct the spelling of --polymethylene--; same column, Claim 4, line 36, delete "component" and insert --and--.

Signed and Sealed this

Twentieth Day of July 1976

[SEAL]

Attest:

RUTH C. MASON
Attesting Officer

C. MARSHALL DANN
Commissioner of Patents and Trademarks